(12) United States Patent
White et al.

(10) Patent No.: US 7,913,959 B2
(45) Date of Patent: Mar. 29, 2011

(54) MEDICAL/DENTAL SUCTION NOZZLE HOLSTER HAVING A UNIVERSALLY ADJUSTABLE STRAP

(75) Inventors: Lynn R. White, Denver, CO (US); Paul Burek, Centennial, CO (US)

(73) Assignee: Patient Shield Concepts, LLC, Denver, CO (US)

( * ) Notice: Subject to any disclaimer, the term of this patent is extended or adjusted under 35 U.S.C. 154(b) by 650 days.

(21) Appl. No.: 12/028,575

(22) Filed: Feb. 8, 2008

(65) Prior Publication Data

US 2009/0202960 A1 Aug. 13, 2009

(51) Int. Cl.
*A62C 13/76* (2006.01)

(52) U.S. Cl. .......................................... 248/79; 248/314

(58) Field of Classification Search .................. 248/314, 248/313, 213.2, 309.1, 230.8, 79; 128/852; 220/476, 480, 676; 224/251
See application file for complete search history.

(56) References Cited

U.S. PATENT DOCUMENTS

| | | | |
|---|---|---|---|
| 1,096,180 A | 5/1914 | Meurling | |
| 2,014,241 A | 9/1935 | Ness | |
| 3,371,897 A | 3/1968 | Serany, Jr. et al. | |
| D231,031 S | 3/1974 | Hinnenkamp | |
| 4,061,226 A | 12/1977 | Essen | |
| 4,076,199 A | 2/1978 | Paulsen | |
| 4,085,755 A | 4/1978 | Burrage | |
| 4,170,234 A | 10/1979 | Graham | |
| 4,272,047 A * | 6/1981 | Botka | 248/74.3 |
| D282,684 S | 2/1986 | Cline | |
| 4,597,551 A | 7/1986 | Ciechanowski et al. | |
| 4,773,768 A | 9/1988 | Leeper | |
| 4,805,856 A | 2/1989 | Nicoli et al. | |
| 4,880,413 A | 11/1989 | Giuffre et al. | |
| 5,135,188 A * | 8/1992 | Anderson et al. | 248/74.3 |
| 5,188,327 A | 2/1993 | White | |
| 5,224,679 A * | 7/1993 | Code | 248/314 |
| D346,243 S | 4/1994 | Weber | |
| 5,584,452 A | 12/1996 | Koike | |
| 5,634,569 A | 6/1997 | DeCoster | |
| D381,847 S | 8/1997 | Shingles | |
| 5,669,564 A | 9/1997 | Keller et al. | |
| 5,752,286 A | 5/1998 | Wright | |
| 5,775,653 A * | 7/1998 | Horney et al. | 248/230.8 |
| 5,806,822 A | 9/1998 | Schulz | |
| 5,906,302 A * | 5/1999 | Spergel | 224/250 |
| 5,915,583 A | 6/1999 | Cloonan et al. | |
| 5,915,963 A | 6/1999 | Homra | |
| 5,927,974 A | 7/1999 | Homra | |
| D415,917 S | 11/1999 | Salazar et al. | |
| 6,077,074 A | 6/2000 | Homra | |
| D435,104 S | 12/2000 | Urueta et al. | |
| 6,206,258 B1 * | 3/2001 | Calder | 224/420 |
| 6,367,110 B1 | 4/2002 | Urueta et al. | |
| D463,698 S | 10/2002 | Phillips et al. | |
| D500,703 S | 1/2005 | Giampavolo | |
| D501,886 S | 2/2005 | Chen et al. | |
| D533,343 S | 12/2006 | Gringer | |

(Continued)

*Primary Examiner* — Ramon O Ramirez
(74) *Attorney, Agent, or Firm* — Dorr, Carson & Birney, P.C.

(57) ABSTRACT

A suction nozzle holster is provided with a latch mechanism for receiving a universally adjustable strap having a groove system whose individual grooves can engage with a pawl of a lever arm of said latch mechanism. A forward surface of the holster may be provided with a hole into which a suction hose can be forced in order to constrict said hose and, hence, curtail the vacuum conditions in a suction nozzle serviced by that hose.

21 Claims, 12 Drawing Sheets

U.S. PATENT DOCUMENTS

| | | |
|---|---|---|
| D541,933 S | 5/2007 | White et al. |
| D572,625 S | 7/2008 | Doan |
| 2005/0194507 A1 | 9/2005 | White |
| 2005/0230280 A1 | 10/2005 | Sotiropolous et al. |
| 2006/0032769 A1 | 2/2006 | Erickson et al. |
| 2006/0192064 A1 | 8/2006 | White et al. |
| 2006/0229567 A1 | 10/2006 | Wright |
| 2007/0023586 A1 | 2/2007 | Geiger |
| 2007/0057129 A1 | 3/2007 | White et al. |
| 2007/0199846 A1 | 8/2007 | Wright |
| 2008/0264992 A1* | 10/2008 | Westling ................ 224/673 |

* cited by examiner

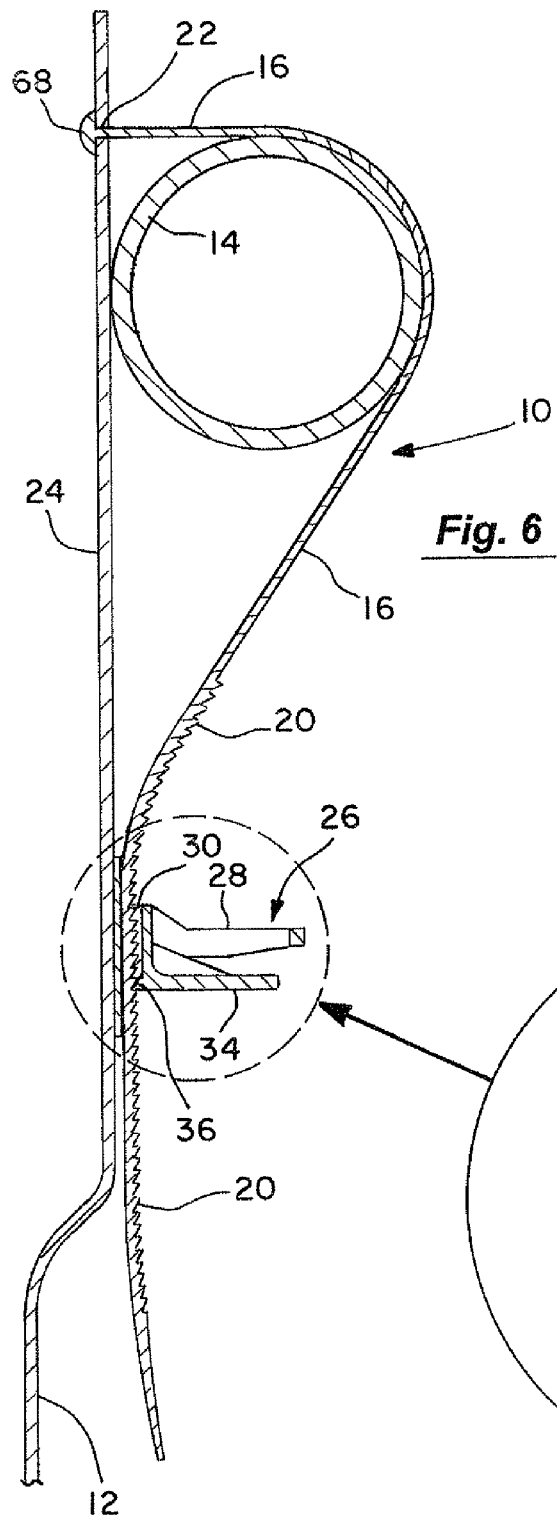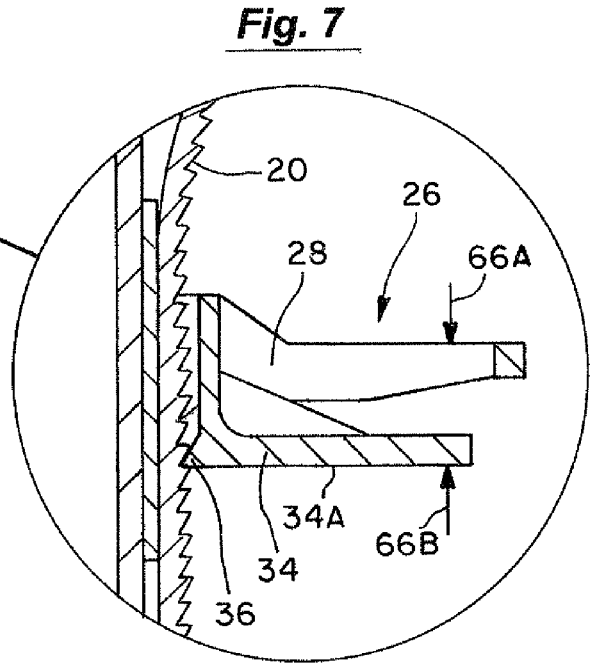

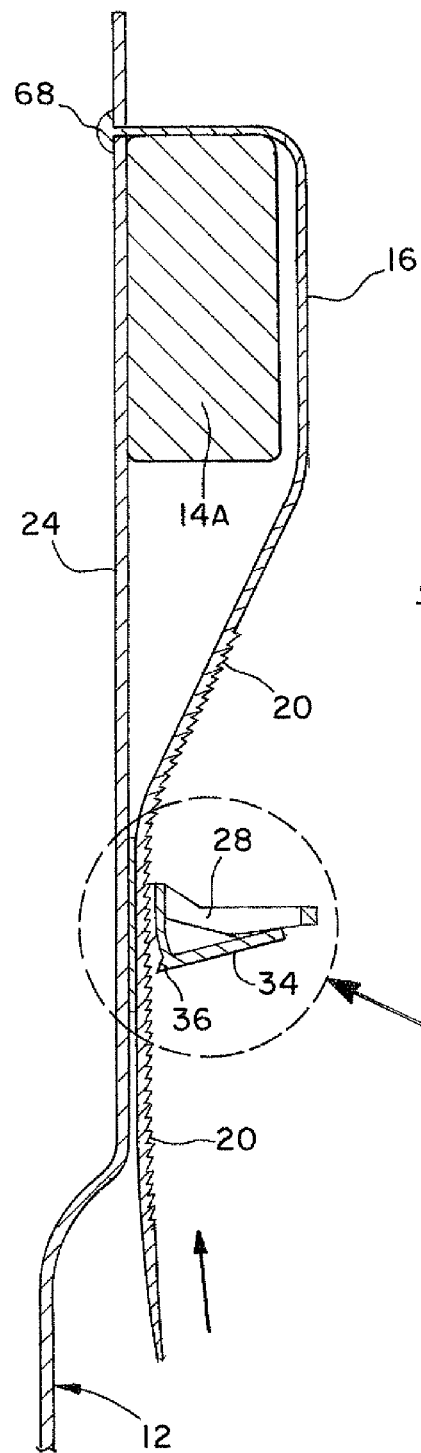
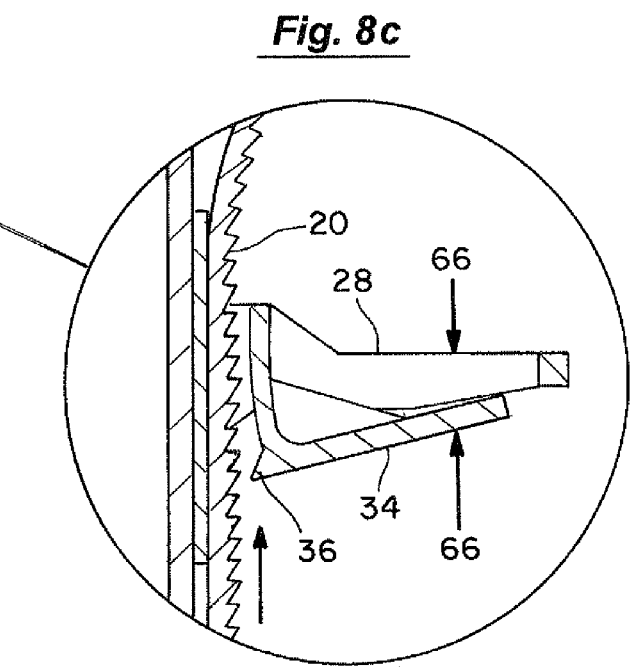
*Fig. 8b*
*Fig. 8c*

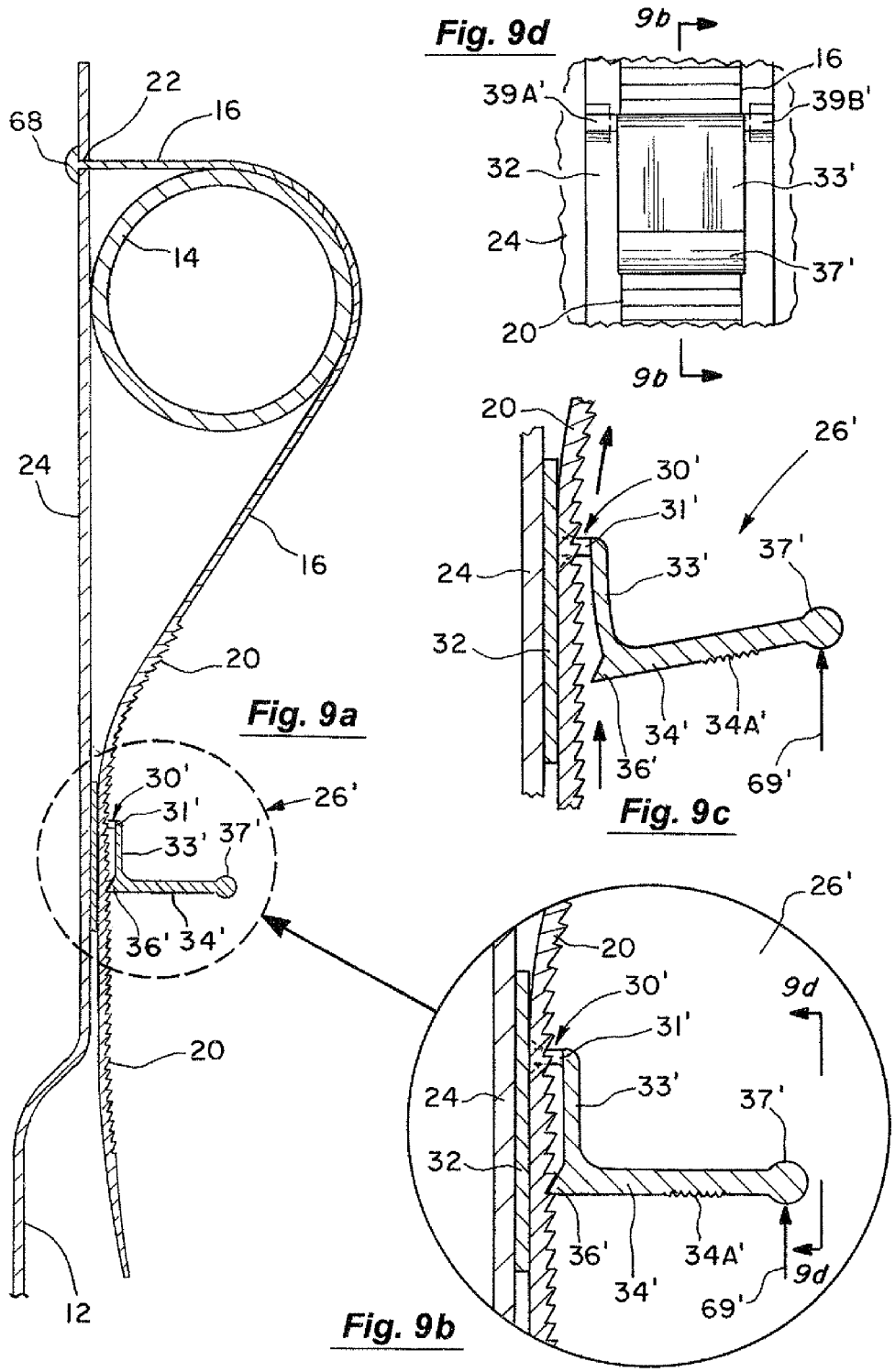

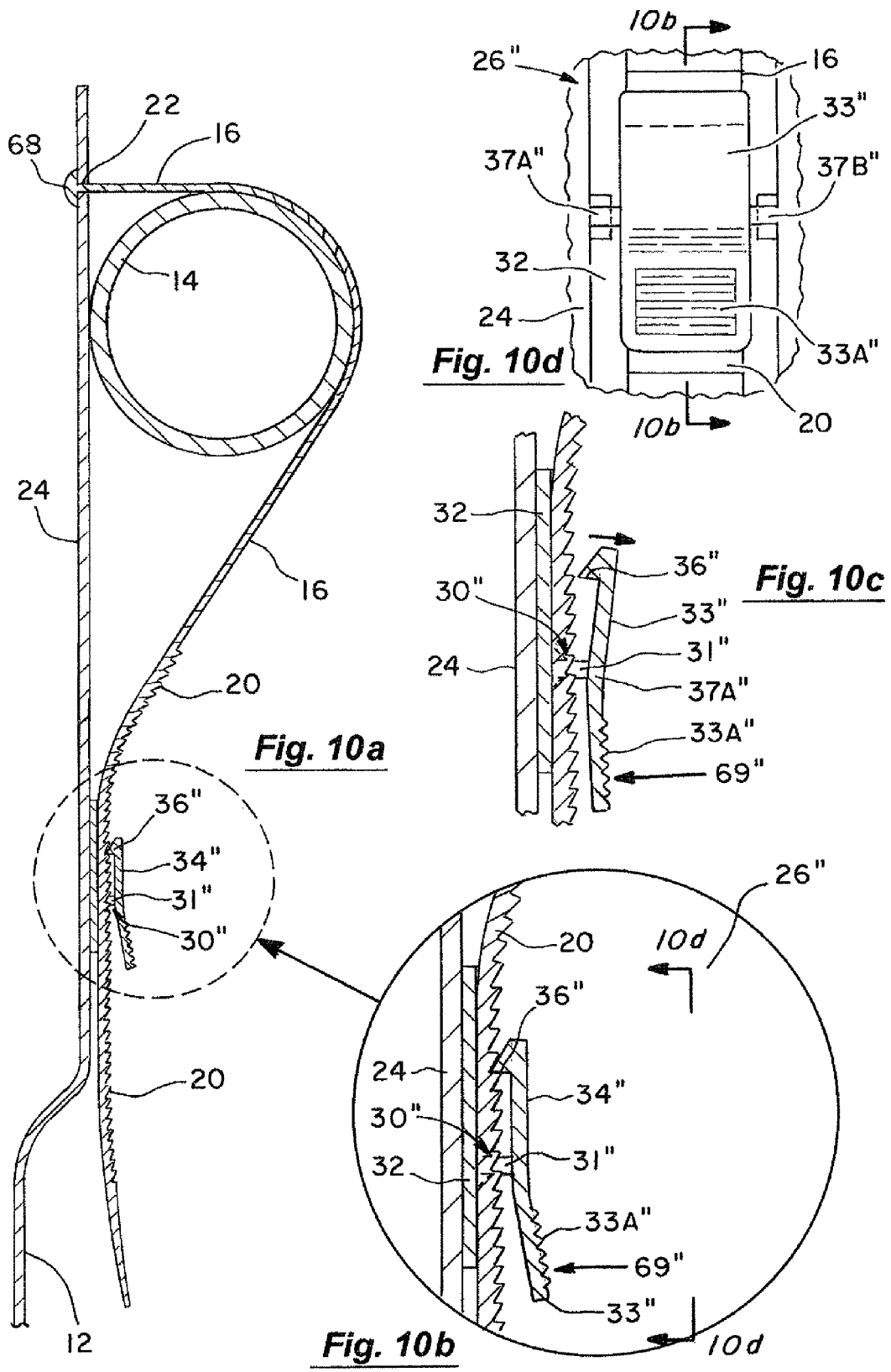

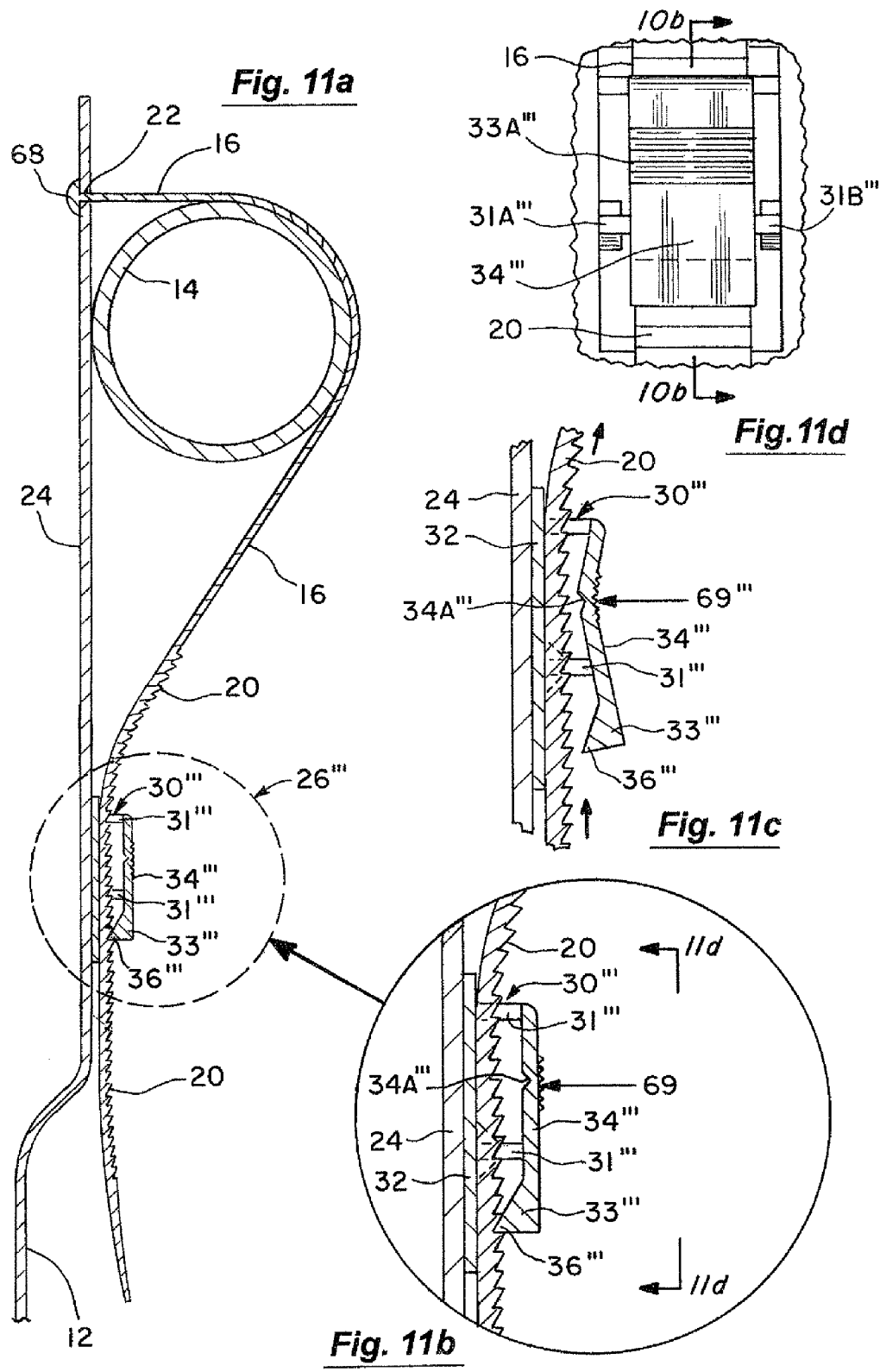

MEDICAL/DENTAL SUCTION NOZZLE HOLSTER HAVING A UNIVERSALLY ADJUSTABLE STRAP

BACKGROUND OF THE INVENTION

1. Field of the Invention

This invention is generally concerned with holsters for the nozzle components of medical/dental suction devices such as so-called Yankauer® suction tubes. Use of these holsters serves to maintain aseptic conditions and convenient human hand access to such suction devices during medical/dental procedures. Applicants' invention is particularly concerned with: (1) use of a universal strap (a strap capable of snugly fitting around any bedrail or like object, no matter what its size or cross sectional configuration) and (2) use of a latch mechanism having a bendable (or rotatable) lever arm that terminates in a pawl which cooperates with a groove system on the universal strap and (3) use of a hole in a forward surface of the holster body to pinch a flexible suction hose that leads to the suction tube so that the partial vacuum conditions that exist in the hose can be, on a temporary basis, substantially curtailed or completely cut off.

2. Discussion of the Background

A wide variety of medical/dental suction nozzle holsters are disclosed in the patent literature. Such holsters have many different features that perform various distinct technical functions as well as various convenience-in-use functions. These convenience-in-use functions often involve the use of special mechanical devices to attach such nozzle holsters to a bedrail or operating table rail or similar object for ease and/or convenience of use during medical/dental procedures wherein the medical/dental practitioners attention is often urgently directed away from such holsters. These prior art suction nozzle holsters have for example employed so-called C-clamps, alligator jaw devices, Velcro® strips and the like to attach a holster to an operating table, bed, etc. Other known holster attachment devices use nub and groove systems to hold a holster, and hence the nozzle held in it, in one of three distinct operating positions.

However, none of these prior art medical suction nozzle holsters provide a strap that is capable of snugly fitting equally well over and around bedrails having rectangular, round or square cross sectional configurations or readily engaging and disengaging with a latch that forms a part of the holster body and thereby creating a more snug abutment between the holster and the bedrail relative to those abutments that can be achieved using straps having belt buckle type tightening devices wherein one end of a strap attaches to the other end of that strap. A brief review of the prior art is as follows.

U.S. Patent Publication No. US 200710057129 A1 ("the '7129 patent publication") teaches a suction nozzle holster capable of three distinct operating positions. These three positions are made possible through selective use of two main holster mounting components. The first component is a holster mounting mechanism that further comprises a rear plate having an elongated groove for receiving an elongated nub. The second component is a mounting channel. The face side of this mounting channel is provided with three separate and distinct key plate/key nub systems. Each of these key plate/key nub systems may be readily inserted into (or removed from) the keyway slot/nub receiver opening system located in the rear plate of the holster mounting mechanism. This holster also features an upper rim that is provided with a V-shaped notch into which a suction hose can be forced in order to constrict the hose and, hence, curtail the vacuum conditions in a Yankauer® type suction nozzle.

U.S. Pat. No. 4,773,768 ("the '768 patent") teaches a suction tube retaining and disposal container. It comprises: (1) a mounting board that can be inserted between a mattress and frame of a hospital bed, (2) a disposable bag and (3) a second board having an aperture into which a bent over portion of a flexible suction tube can be inserted in order to stop any liquid flow out of an open end of the flexible suction tube.

U.S. Patent Publication No. 2006/0192064 A1 ("the '2064 patent publication") teaches a suction nozzle holster capable of three operating positions. These three positions are made possible through selective use of two main holster mounting components. The first component is a holster mounting mechanism that further comprises a rear plate having a groove for receiving a nub. The second component is a mounting channel. The face side of this mounting channel is provided with three separate and distinct key plate/key nub systems. Each of these key plate/key nub systems may be readily inserted into (or removed from) the keyway slot/nub receiver opening system located in the rear plate of the holster mounting mechanism. U.S. Design Pat. No. 541,933 S teaches the same nozzle holster.

U.S. Patent Publication No. 2005/0194507 A1 ("the 4506 patent publication") teaches use of a suction nozzle holster that employs an array of individually usable sterile sacs.

U.S. Design Pat. No. 282,684 ("the '684 patent") teaches a cup for an electrosurgical cautery pencil. The cup is mounted (e.g., to a wall) by use of a horizontal slot.

U.S. Design Pat. No. 231,031 ("the '031 patent") teaches an active cautery electrode holder that is mounted by use of a horizontally extending plate.

U.S. Design Pat. No. 500,703 S ("the '703 patent") teaches a flower bouquet holder having a U-shaped holder device.

U.S. Pat. No. 5,188,327 ("the '327 patent") teaches a holder for an attendant (e.g., nurse) signaling device. The device is held to a bedrail by a pair of resilient C-clamp members.

U.S. Design Pat. No. D 533,343 S ("the '343 patents") teaches a tool sheath that has an inverted "U" shaped attachment device.

U.S. Pat. No. 4,597,551 ("the '551 patent") teaches a surface-mounted apparatus for holding a hand-held instrument (such as a suction nozzle) when not in use. This apparatus has an elongated cylindrical shell having a longitudinal slot for receiving the hand-held instrument and a mounting plate.

U.S. Pat. No. 4,076,199 ("the '199 patent") teaches an apparatus for clamping cables in rows and columns between rigid bars having a plurality of slots. Flexible plastic straps having teeth along their lengths cooperate with teeth in the slots of the bars to form a ratcheting lock device.

U.S. Pat. No. 4,085,755 ("the '755 patent") teaches a fluid drainage bag having a flap valve in a fold. The fold is held open by means of a flexible drainage tube held in a flexed position between the fold and the upper end of the bag.

U.S. Pat. No. 5,584,452 ("the '452 patent") teaches a harness clip having a band that continuously extends from a front face of a flange portion of said harness clip. The band is further provided with a plurality of projections (e.g., nubs on the top surface of the band) that function as stops when engaged with a pair of stopper claws and with a lock piece.

U.S. Pat. No. 4,805,856 ("the '856 patent") teaches a cable mount having a strap having a row of teeth disposed along its inner surface. A locking pawl is formed within a strap-receiving opening. It engages with a given tooth of the row of teeth on the strap.

U.S. Pat. No. 4,170,234 ("the '234 patent") teaches a cup for an electrosurgical pencil. The cup is attached to a surgical drape by means of a drape clamp.

U.S. Pat. No. 3,371,897 ("the '897 patent") discloses a drain bag support assembly having a yoke that further comprises a strap that goes around a bedrail. The attachment means comprises opposed notches 24 that extend transversely from the longitudinal edges of the strap. The notches engage the edges of an opening in the drain bag support.

U.S. Pat. No. 4,272,047 ("the '047 patent") teaches a support clamp for bundles of wire or hydraulic lines. It further comprises a strap having lateral teeth on one side. The strap is integral with a head having an opening for receiving the strap. A further component of the head is a resiliently pivotable element having teeth that engage with the teeth on the strap to create a clamping effect.

U.S. Pat. No. 5,669,564 ("the '564 patent") teaches an apparatus for winding a strand into a multilayered package.

U.S. Pat. No. 6,367,110 B1 ("the '110 patent") teaches a holster for an electrocautery tip. The holster is attached to an operating table, Mayo instrument table, etc. by a temporary attachment means such as a spring-loaded, wide-base C-clamp (see FIGS. 4a and 4b) or a releasable clip (see FIG. 4). U.S. Design Pat. No. 324,104 teaches the same device.

U.S. Pat. No. 5,752,286 ("the '286 patent") discloses a cleaning and storage device for an aspirator instrument such as a Yankauer suction tube. The device has a holder that can be attached to a bedrail by opposing adhesive surfaces or by a C-shaped clamp.

U.S. Pat. No. 5,806,822 ("the '822 patent") discloses a wall mounted holder for a Yankauer suction instrument. The holder has a base and two spaced supports respectively extending substantially horizontally from the upper end of the vertically mounted base and from the lower end of said base. The upper support may comprise, for example, a continuous rim that forms an annular ring that defines an opening for receiving the forward end of a suction instrument and thereby preventing it from tipping laterally. The lower support preferably has two spaced support arms that define a substantially horizontal slot. In effect an upper end of the suction device resides in the ring while the handle portion of the suction device rests on the support arms above the slot while a suction hose portion of the suction device extends through the horizontal slot defined by the two spaced apart support arms.

U.S. Pat. No. 6,077,074 ("the '074 patent") discloses a sleeve-type holder for a suction device such as a Yankauer suction tube. One end of a sleeve component of this holder is provided with a frame that can be slidably mounted to a C-shaped frame track having a compatible C-shaped channel configuration. The opposing end of the sleeve is provided with a hole for receiving a hook of a body member bar. The body member bar is attached to a clamp that attaches the bar, frame and sleeve assembly to a bedrail.

The teachings of U.S. Pat. No. 5,927,974 ("the '974 patent") are quite similar to those of the '074 patent. It does, however, contain the added feature (see FIGS. 10 and 11) of providing the frame with a dovetail side that is inserted into a dovetail track (i.e., dovetail-shaped channel).

The teachings of U.S. Pat. No. 5,915,963 ("the '963 patent") are similar to those of the '974 patent. The main difference between these two patent references is depicted in FIGS. 17 and 18 of the '963 patent. They show a frame-like member hingedly mounted to a mounting plate. This plate is fixedly mounted to a clamp that is, in turn, slidably mounted to a bedrail or similar bar-like object.

U.S. Pat. No. 5,224,679 ("the '679 patent") teaches a holster for a hand-held instrument such as an intake nozzle of an operating room suction device. The '679 patent suggests several ways the holster may be attached to an operating table (see FIGS. 1, 4 and 5). These ways include: (a) blade-like inserts for placement between table tops and cushions, alligator clamps and C-clamps having hand operable tightening/loosening bolts. This holster is adapted to hold a bubble wrap in which the suction device was originally packaged. The suction tip is holstered in this original package during use. The nozzle holster also is adapted to secure the bubble wrap to the inside of the holster. After the operation is over, the wrapper and nozzle are disposed of and a new nozzle-containing wrapper (e.g., clear plastic bag) is put in the holster.

SUMMARY OF THE INVENTION

The medical/dental suction nozzle holster devices of this patent disclosure are particularly characterized by the fact that they are held to a bedrail, operating table rail and the like by a strap that can readily accommodate to the shape and size (up to about 3.5 inches in diameter) of such rails—be they rectangular, round or square. Applicants choose to call such a strap a "universal strap" or, owing to its flexible nature, a "flexible, universally adjustable strap." It might also be noted here that for purposes of this patent disclosure. Applicants will use the expression "bedrail" to describe the type of rail to which their holster will usually be attached. Use of this term is however intended to include comparable rails on operating tables, gurneys, etc., as well as other commonly available medical equipment such as tables and trays. In any case, use of Applicants' universal strap will cause the holster to hang in a substantially vertical orientation. In this vertical orientation, the nozzle's handle portion will naturally tilt to one side or the other of the holster rim and thereby provide convenient hand access to said nozzle handle.

Next, it should be noted that the universal straps of this patent disclosure can be readily operated without the use of hand tools or hand tightening knobs that cooperate with threaded bolts—which sometimes undergo untoward loosening during use. Most medical practitioners will be able to easily operate Applicants' universal strap devices with the power provided by their thumb and index finger. As will be better seen in various figures of the present invention (e.g., FIGS. 8a and 8b), this ease of operation is made possible through use of a latch mechanism having a flexible (or rotatable) lever arm component that can be bent (or rotated) by human thumb/finger pressure. This flexible (or rotatable) lever arm component can have a horizontal orientation or a vertical orientation. In either case, the flexible (or rotatable) lever arm component terminates in a pawl. After the universal strap is pulled downward to a desired state of tension, the pawl end of the flexible (or rotatable) lever arm can be placed in contact with (or taken out of contact with) a given groove of a groove system that is located on the leading end of the top surface of Applicants' universal strap. In other words, the pawl engagement with a given groove of the universal strap is achieved by pulling the ratchet-like grooves of the strap past the pawl and/or by releasing pressure (provided by thumb/finger pressure) on a temporarily bent (or rotated) flexible lever arm and thereby allowing the pawl to engage with (or disengage from) a particular groove of the groove system. Thus, the groove system serves as the means for adjusting the snugness of the universal strap around the rail to which the holster is attached. In effect the strap's groove system serves as a rack that is selectively associated with the pawl of the flexible lever arm to create a ratchet device. Once the pawl is placed in a selected groove it is firmly held there by the ratchet effect created by the geometry of the individual grooves of the groove system vis-à-vis the front end of the pawl (see for example FIG. 7).

It might also be noted here that an appropriate under surface, or an appropriate upper surface, of the flexible (or rotatable) lever arm component of the latch mechanism also can be given a roughened surface to prevent thumb/finger slippage from this lever arm surface. These thumb/finger contact enhancing features are not essential to the use of this medical/dental suction nozzle holster device, but they are practical optional features. This follows from the fact that such holster devices are often mounted to a side rail (and dismounted from such a rail) by hands residing in wet surgical gloves.

An additional feature of Applicants' suction nozzle holsters is its use of a hole in a forward surface of the holster body. Such a hole serves as a means of temporarily pinching off the suction conditions in the flexible suction hose component of these medical/dental suction devices. In any case, the hole in the forward surface of Applicants' holster body should be wide enough (e.g., from about 0.5 to about 1.25 inches) to accept two portions of the outside diameter of most commonly available suction hoses. For example, many commonly available suction hoses have outside diameters ranging from about 0.75 inches to about 1.25 inches. In any case, the holes in the holster body will normally have a circularly-shaped or elliptically-shaped configuration. They might however also have a square, rectangular or hexagonal configuration. Applicants will use the expression "shaped hole" to describe all of these possible hole configurations. It might also be noted here that the ability of a medical/dental practitioner to curtail the suction action at the holster—as opposed to turning a shut off valve on a vacuum creating device (aspirator) that is typically located much further away from the patient—has a great deal of convenience-in-use value. That is to say that the hole in Applicants' holster enables a medical practitioner to more conveniently shut off the suction action while said practitioners attention is still directed toward a nearby patient. There also may be times during the course of a medical procedure that the medical staff needs to converse in a relatively quiet atmosphere. Because suction tubes make clearly discernable aspirating sounds that are annoying, distracting and/or not conducive to quiet conversations, it is of considerable advantage to have the ability to temporarily eliminate such sounds without having to leave the immediate vicinity of the patient to turn a shut off valve at a somewhat distant aspirator device.

BRIEF DESCRIPTION OF THE DRAWINGS

FIG. 6 is a side view of a universal strap going over and around a round bedrail, through an opening in a first representative latch mechanism and then engaging with a pawl of a bendable (or rotatable) lever arm of that first representative latch mechanism.

FIG. 7 is an enlarged side view of the first representative latch mechanism detailing the engagement of the pawl and a strap groove.

FIG. 8b shows a first representative lever arm about to be bent (or rotated) upward to disengage the pawl from a groove in the groove system and thereby releasing the strap from the bedrail.

FIG. 8c is a detail of the disengagement of the pawl of the first representative lever arm from a groove of the strap.

FIG. 9a is a side view of a universal strap going over and around a round bedrail, through an opening in a second representative latch mechanism and engaging with a pawl of a bendable (or rotatable) lever arm of that second representative latch mechanism.

FIG. 9b is an enlarged side view of the second representative latch mechanism detailing the engagement of the pawl and a strap groove.

FIG. 9c depicts the second representative latch mechanism in the absence of the universal strap.

FIG. 9d is a top view of the second representative latch mechanism.

FIG. 10a is a side view of a universal strap going over and around a round bedrail, through an opening in a third representative latch mechanism and engaging with a pawl of a vertically mounted, bendable (or rotatable) lever arm of that third representative latch mechanism.

FIG. 10b is an enlarged side view of the third representative latch mechanism detailing the engagement of the pawl and a strap groove.

FIG. 10c depicts the third representative latch mechanism in the absence of the universal strap, FIG. 10d is a top view of the third representative latch mechanism.

FIG. 11a is a side view of a universal strap going over and around a round bedrail, through an opening in a fourth representative latch mechanism and engaging with a pawl of a vertically mounted, bendable (or rotatable) lever arm of that fourth representative latch mechanism.

FIG. 11b is an enlarged side view of the fourth representative latch mechanism detailing the engagement of the pawl and a strap groove.

FIG. 11c depicts the fourth representative latch mechanism in the absence of the universal strap.

FIG. 11d is a top view of the fourth representative latch mechanism.

DETAILED DESCRIPTION OF THE INVENTION

Figure 1:
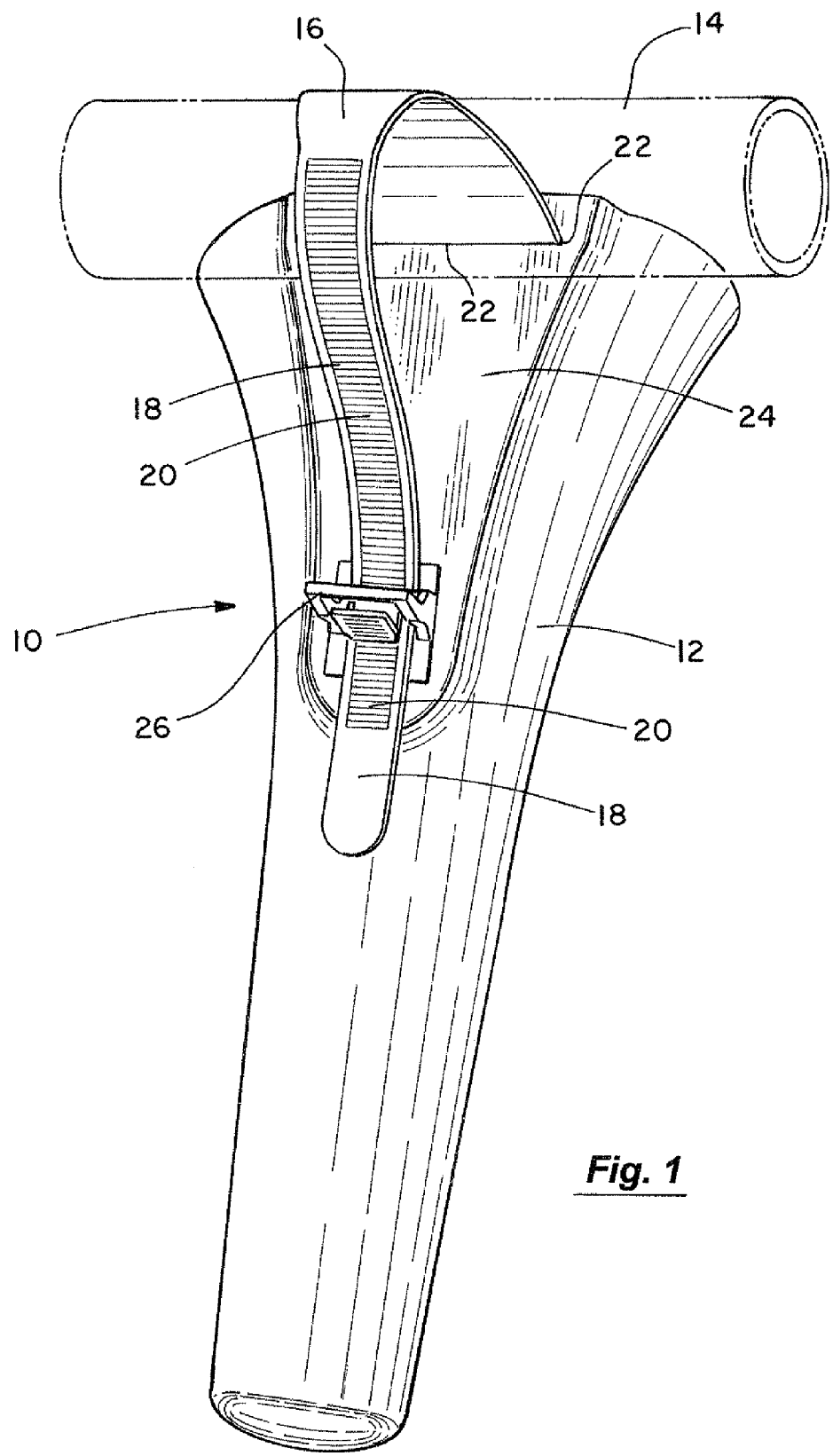
FIG. 1 is a perspective view of the rear side of the medical/dental suction nozzle holster device of this patent disclosure shown mounted to a side rail of an operating table using an embodiment of Applicants' latch mechanism.
Figure 3:
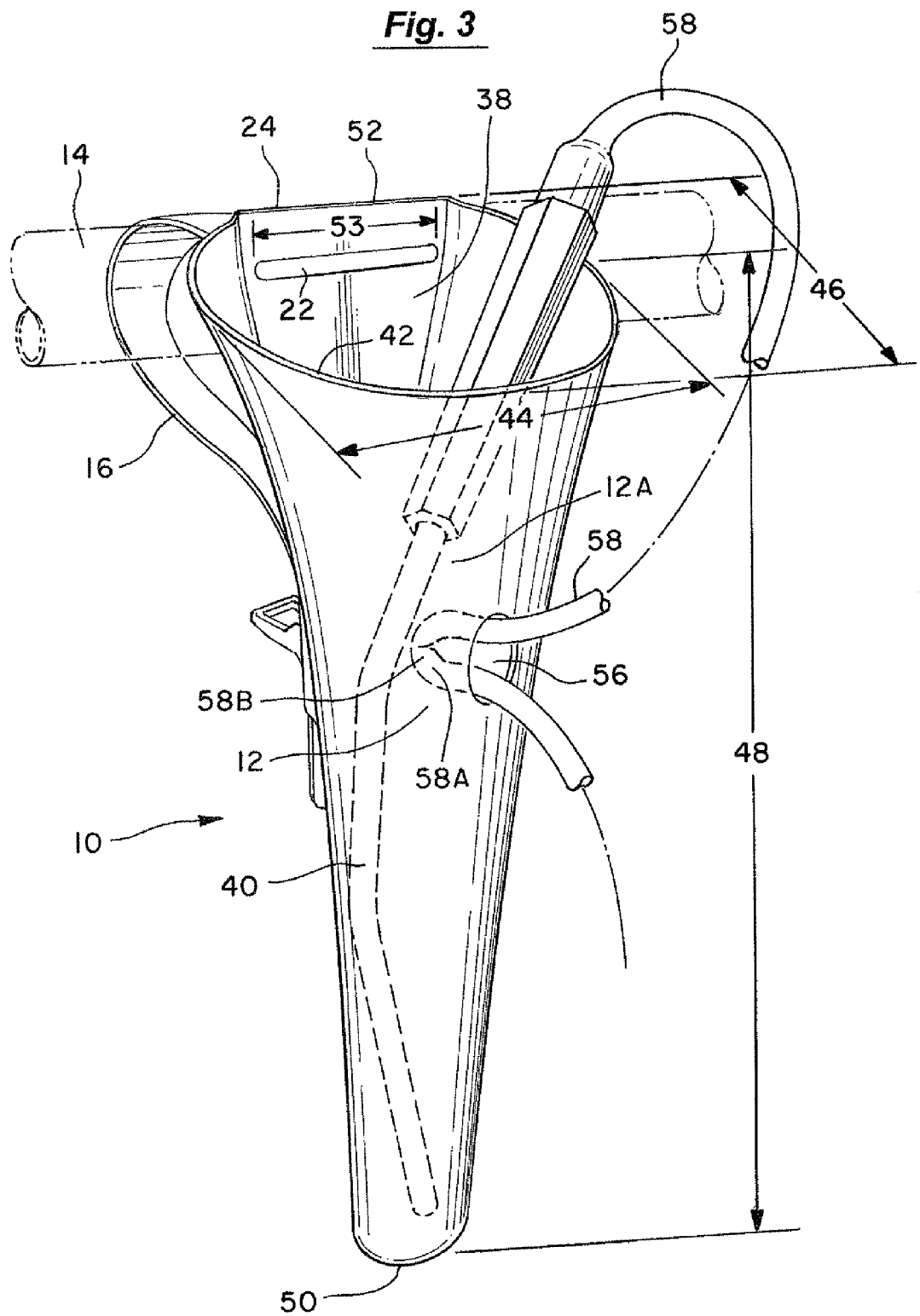
FIG. 3 is a front perspective view of a representative embodiment of a suction nozzle holster of this patent disclosure. It is shown: (1) attached to an operating table having a round side rail by use of Applicants' universal strap, (2) holding a Yankauer nozzle and (3) using a hole in the forward surface of the holster for holding a looped portion of the suction nozzle hose that services the Yankauer nozzle.
Figure 4:
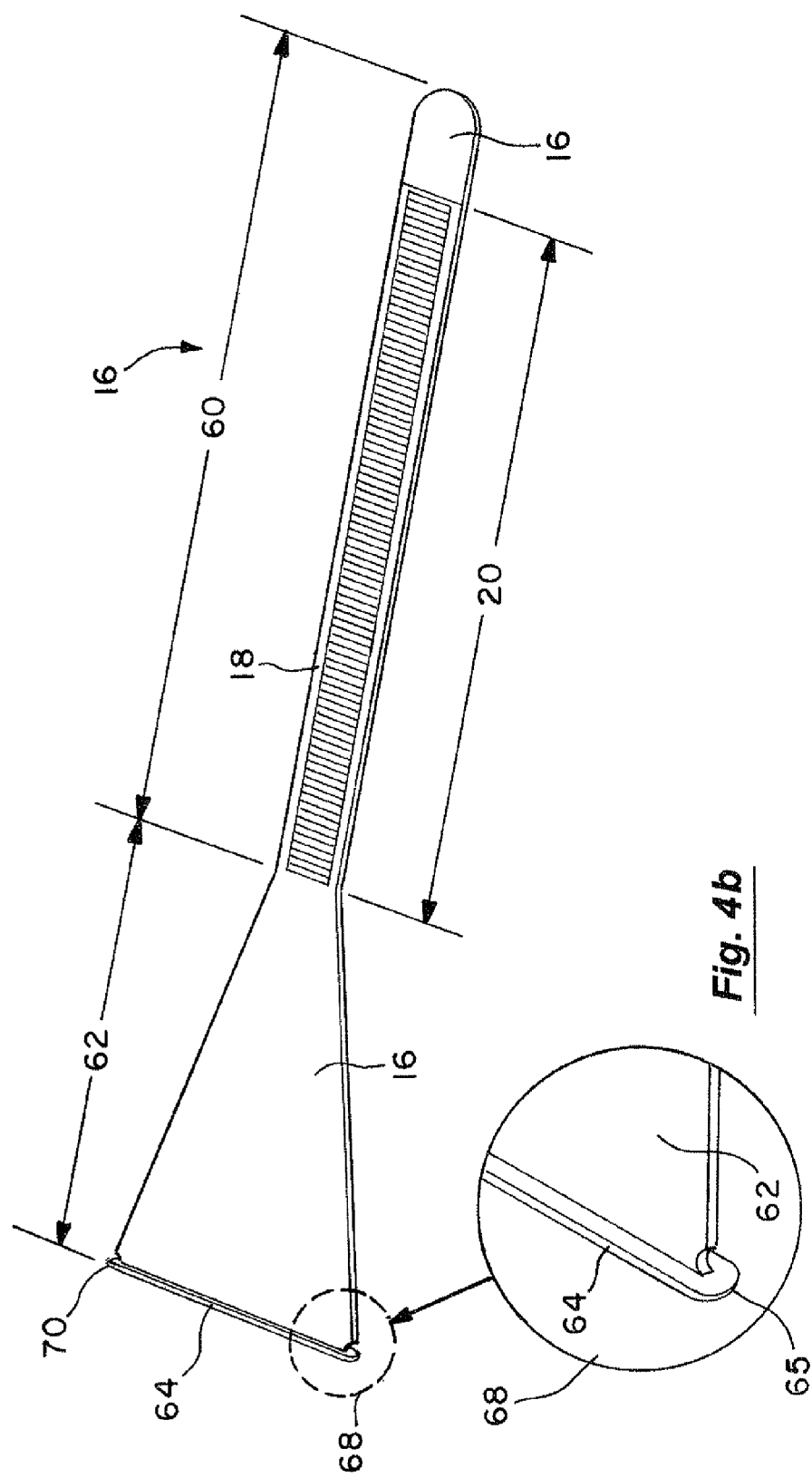
FIG. 4a is a top perspective view of an exemplary universal strap.
FIG. 4b is a detail of an exemplary device for preventing the triangular end of the universal strap from passing through a slot in the holster.

FIG. 1 is a rear perspective view of an exemplary medical/dental suction nozzle holster device 10 of this patent disclosure. Its holster component 12 is shown attached to a bedrail, operating table rail, etc. 14 by means of a universal strap 16. Such rails often have certain sizes and standardized cross sectional configurations. For example, many rails commonly found on operating room tables are round and have diameters of 1.0 to 2.5 inches. Others are rectangular in nature and have a height of about 1.25 inches and a width of about 0.3125 inches. Other rail dimensions and cross section geometries (e.g., square, etc.) are of course also possible. Be that as it may, a leading portion of the top side 18 of the universal strap 16 is shown provided with a groove system 20. The universal strap 16 is shown penetrating through a rectangular slot 22 in the rear side 24 of the holster component 12. This slot 22 has a width that is slightly greater than the thickness of the leading portions of strap 16 and thereby allowing passage of leading portions of the strap 16 through the slot 22. The trailing portions of the strap 16 can be thicker than the width of the slot 22 and thereby preventing complete passage of the trailing portions of the strap 16 (see for example, FIGS. 4b, 6 and 7). As seen in FIG. 3, the length of the slot 22 is slightly less than the trailing portions of a triangular rear end of the strap 16 (which is further illustrated in FIGS. 4 and 5). A leading portion of the strap 16 (which is provided with the groove system 20) is shown passing through a rectangular opening in a latch mechanism 26 shown in FIG. 1.

Figure 2:
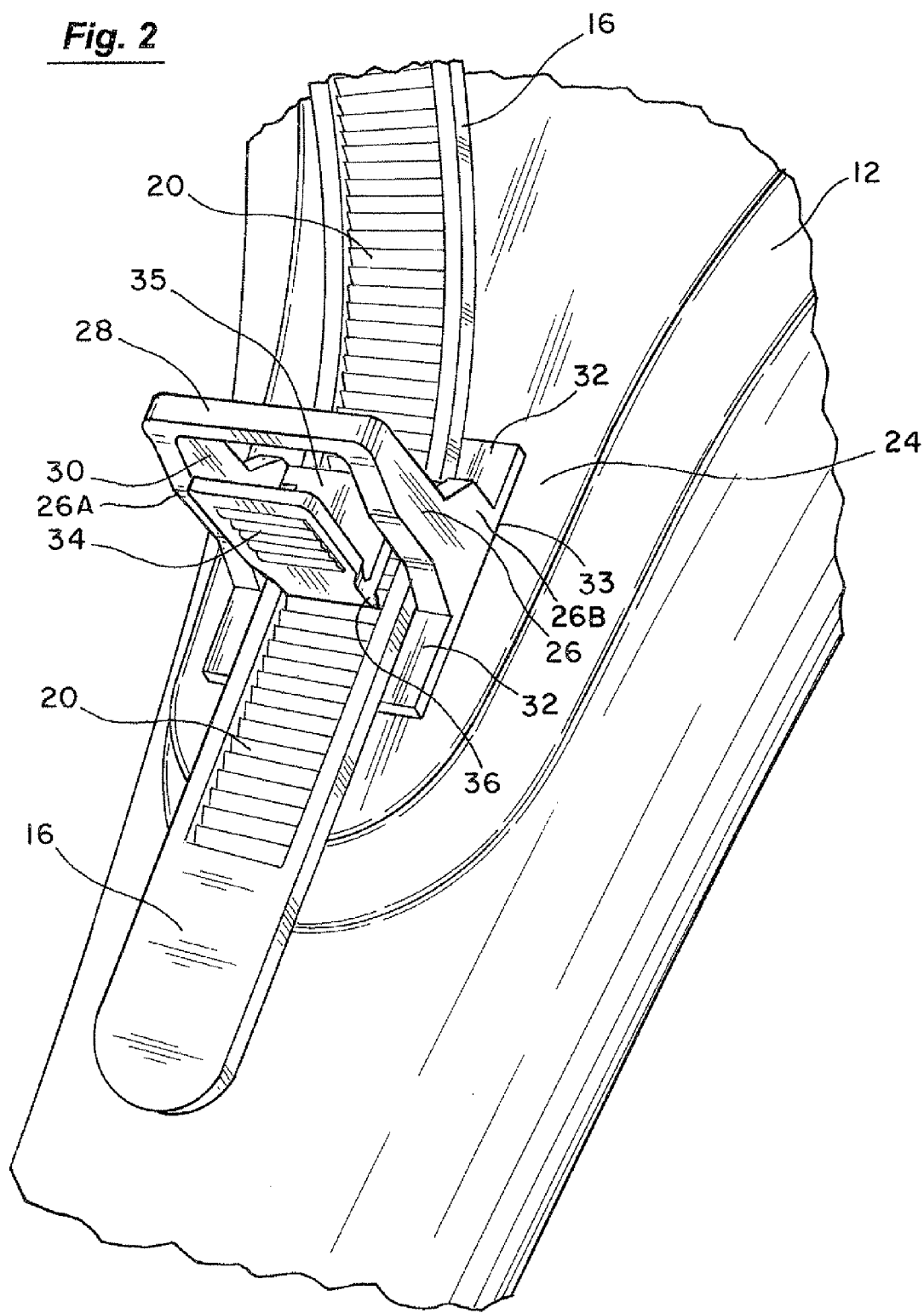
FIG. 2 is an enlarged perspective view of a representative latch mechanism that receives and engages a universal strap component of this invention.

FIG. 2 is an enlarged perspective view of the latch mechanism 26 attached to the rear side 24 of the holster component 12. The latch mechanism 26 has two side walls 26A and 26B. It also has a top plate 28 having a rectangular opening 30 through which the leading portions of the universal strap 16 have passed. The rectangular opening 30 is located between the front wall 32 of a base plate 33 and a vertical element 35 (as better seen in FIG. 8d) that leads into and becomes a part of a lever arm 34. The rear wall of the base plate 33 is affixed to the rear side 24 of the holster component 12. For example, the rear wall of the plate 33 can be heat fused to or glued to the rear side 24 of the holster component 12. The lever arm 34 is bendable (or rotatable) and terminates in a pawl 36. As seen in FIGS. 6 and 7 this pawl 36 engages with and disengages from a given, operator selected, groove of the groove system 20 on the universal strap 16 and thereby holds the universal strap (via a given groove/pawl engagement) in a desired state of tension that serves to firmly affix the holster component 12 to a rail (not shown).

FIG. 3 is a front perspective view of a suction nozzle holster device 10 of this patent disclosure shown attached to a bedrail 14. This particular bedrail happens to have a round configuration. Be that as it may, the holster device 10 has a holster component 12 that generally defines an inwardly and downwardly constricted holster cavity 38. This cavity 38 receives the front end of a suction nozzle 40, e.g., a medical suction nozzle of the Yankauer® type. The top lip 42 of the holster component 12 is shown in FIG. 3 as having a generally elliptical configuration. The long diameter 44 of such a generally elliptical configuration will generally be from about 3 to about 6 inches (and preferably from about 4-5 inches). The short diameter 46 of the elliptical configuration will generally be from about 1.5 to about 3 inches (and preferably from about 1.5 to about 2.0 inches). The holster component 12 will have a depth 48 that will range from about 8.0 to about 11.0 inches (and preferably from about 8.5 to about 9.0 inches). The body of the holster component 12 is shown generally tapering downwardly and inwardly to a closed, generally elliptical, closed bottom 50. The long diameter of this rounded bottom will be from about 1.0 to about 2.0 inches (and preferably from about 1.25 to about 1.75 inches) while its short diameter will be from about 0.5 to about 1.25 inches (and preferably from about 0.75 to about 1.0 inches). It might also be noted here that the top lip 42 and/or the closed bottom 50 could have other geometric configurations (e.g., completely circular, rectangular, square, etc.), but Applicants have found that generally elliptical or similarly rounded configurations such as that depicted for the top lip 42 generally better facilitate more accurate human hand placement and withdrawal of suction nozzles in the holster cavity 38 during the course of medical/dental procedures. Holsters having top lips whose front sides are somewhat lower (e.g., from about 1.0 to 1.5 inches lower) than the rear regions of the lip also facilitate suction tube placement in (and/or removal from) the holster. The rear surface 24 of the holster 12 also is shown provided with a flat surfaced, rectangular region 52. The slot 22 projects through a top, rear region of this rectangular region 52. This slot 22 will generally have a length 53 of from about 1.5 to about 2.5 inches in length and be about 1/16 to about 1/4 inches in height. As previously noted, the height of the slot 22 should be sufficient to allow leading portions of the strap 16 (including its groove system 20) to pass through the slot 22. The rear end of a triangular portion of the universal strap (see FIG. 4a), however, should be enlarged to prevent it from passing completely through the slot 22.

A forward surface (e.g., the front side 12A of the holster component 12) is shown in FIG. 3 provided with a shaped hole 56. This shaped hole 56 is shown having a generally circular configuration (an elliptical, square, rectangular, etc. configuration also may be employed). In any case, the longest diameter of the shaped hole 56 will be from about 0.5 to 1.5 inches and preferably about 1.0 inch. A portion 58A of a flexible and compressible suction hose 58 is shown bent into a looped configuration and pushed into the hole 56. This bending action serves to create a constricted region 58S in the interior of the flexible hose 58 and thereby curtailing, shutting off, etc. the vacuum conditions in said hose—and hence in the suction tube 40 (e.g., Yankauer® tube) serviced by that hose. That is to say that this looping of the hose 58 causes the inside surface of the hose 58 to be constricted to such an extent that the opposing inside surfaces of the hose are forced into contact with each other and thereby curtailing or completely shutting off the vacuum conditions otherwise extant in such a hose during use. The ability to easily curtail, partially shut off, totally shut off, etc. the vacuum conditions in the hose—and hence the suction tube—provide the previously noted benefits to a medical practitioner during the course of a medical procedure.

FIG. 3 also depicts a suction tube 40 residing in the holster cavity 38. The top or handle end of the suction tube 40 is shown attached to the flexible and compressible hose 58 of the type commonly used in conjunction with medical/dental suction tubes. Such hoses are connected to an aspirator device (not shown) that serves to create partial vacuum conditions at the lower end of the suction tube 40 and thereby making the tube capable of sucking fluids from a patient's mouth, throat, stomach, etc. Again, the aspirating devices to which the other end of the hose is attached are commonly located away (e.g., 5-10 feet) from the patient.

FIG. 4a is a perspective view of Applicants' universal strap 16. It has an elongated tab region 60, a triangular region 62 and a groove system 20 on the upper surface 18 of said strap 16. Such straps will generally be from about 1/16 to about 1/4 inches thick and be made of a flexible plastic material. The tab region 60 and the front regions of the triangular region 62 are sometimes referred to herein as the "leading portions" of the universal strap 16. These leading portions are capable of passing through the slot 22 in the holster body. In opposition to this ability to pass through the slot 22, the rear portions 64 of the triangular region 62 can be provided with increased thickness and/or one or more stop devices that serve to prevent the strap 16 from being pulled completely through the slot 22 during the strap tensioning process needed to affix the holster to a bedrail. For example, the rear portion 64 of the triangular region 62 can be made greater in thickness than the width of the slot 22 in the holster. Additionally (or in the alternative) the inside perimeters 68 and 70 of the universal strap can be provided protruding stop devices that, due to their size and/or geometries, will not pass through the respective ends of the slot 22. In some embodiments of this invention, the end of the rear end of the triangular portion will be glued or heat fused to the inside perimeter of the slot 22.

FIG. 4B is a detail of the left end 68 of the triangular portion 62 of the universal strap 16+It is, by way of example only, shown provided with a hook configuration 65.

Figure 5:
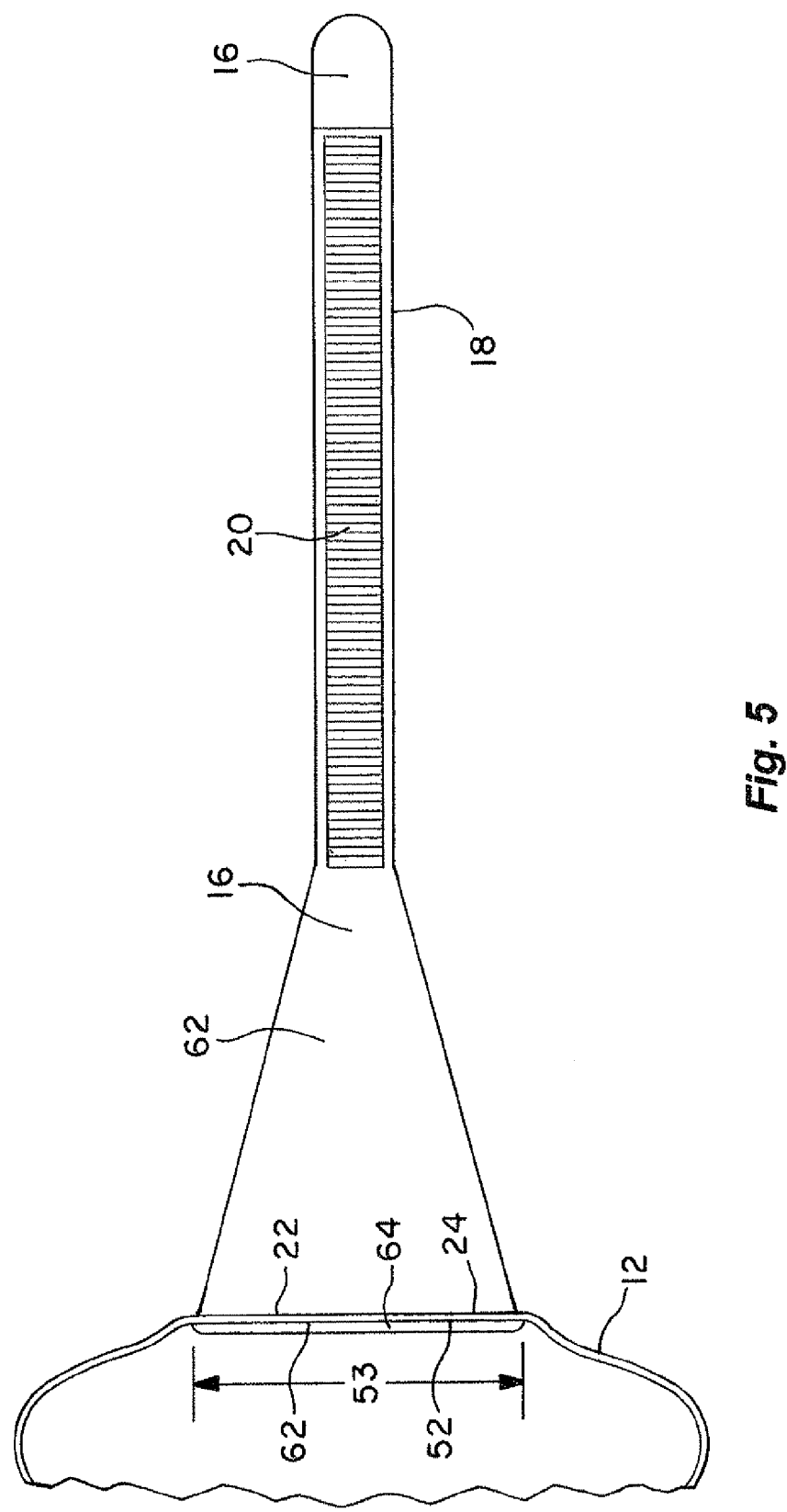
FIG. 5 is a top plan view of a universal strap shown projecting through a slot in the rear wall of Applicants' holster.

FIG. 5 is a top plan view of a universal strap 16 shown projecting through the slot 22 in the holster component 12. FIG. 5 also suggests how the strap can be prevented from being pulled through the slot 22 in one of (or a combination of) several ways. For example, the rear portion 64 of the triangular portion 62 of the strap 16 can be thicker than the height of the slot. Similarly, the width of the rear end of the triangular portion 62 of the strap can be greater than the width 53 of the slot 22. The rear end of the triangular portion can be provided with one or more stop devices (see for example stops 68 and 70 of FIG. 4A) that will come into abutting contact with the holster's rear wall 52. And, as previously noted, a stop on the end of the triangular portion 62 of the universal strap can be glued (or heat fused) to the perimeter of the slot 22.

FIG. 6 is a side cross sectional view of a suction nozzle holster device 10 snugly fitting against a round rail 14. Its universal strap 16 is shown: (1) penetrating through a slot 22 in the rear side 24 of the holster component 12, (2) partially encompassing a bedrail 14, (3) provided with a nub configured stop device 68, (4) passing through a rectangular opening 30 in a top plate 28 of the latch mechanism 26 and (5) being held in a state of tension by the engagement of a pawl 36 on the end of the bendable (or rotatable) lever arm 34 of the latch mechanism 26 with a given groove of the groove system 20.

FIG. 7 is an enlarged detail side view of the latch mechanism 26 that suggests that the lever arm 34 of the latch mechanism 26 can be temporarily bent upward when a substantially vertically directed human thumb/finger pressure (as suggested by the opposing direction arrows designated by items 66A and 66B of FIG. 7) is applied to the bottom 34A of the lever arm 34. This bottom portion 34A of this lever arm 34 can be optionally provided with a roughened surface to prevent thumb/finger slippage during such pressing action. This bending (or rotating) action will be facilitated by the fact that the lever arm 34 is a unitary piece of suitably elastic, plastic material made by a plastic molding operation.

Figure 8A:
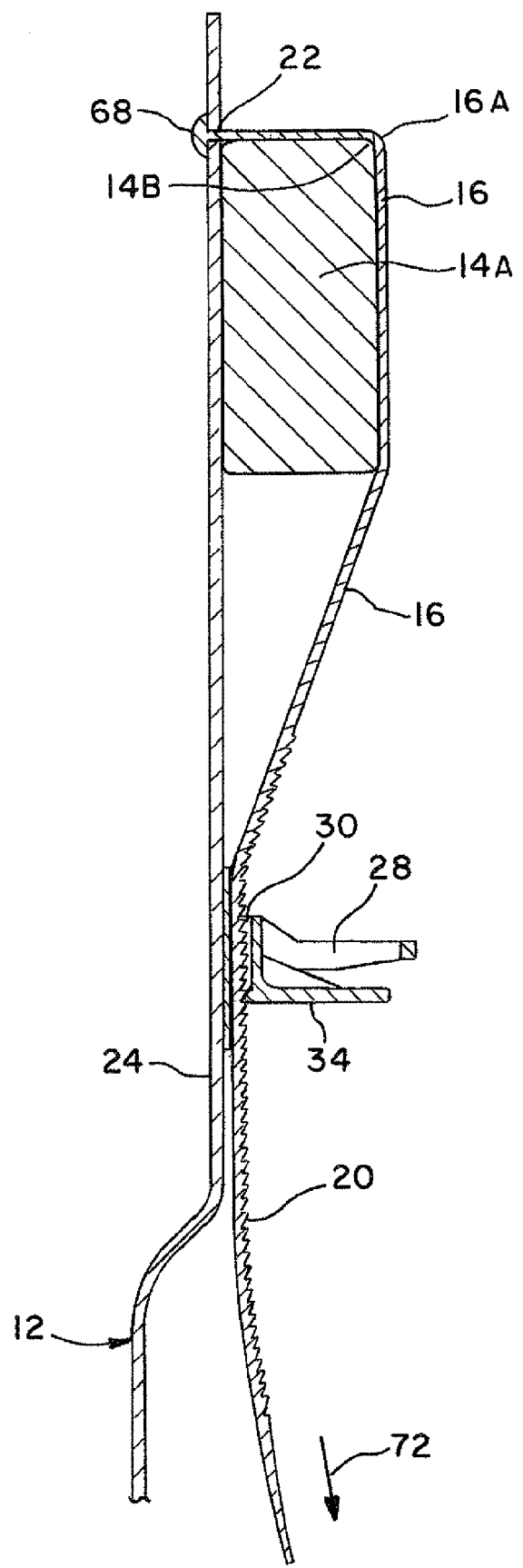
FIG. 8a is a side view of the universal strap going over and around a bedrail having a rectangular cross section and being pulled downward (e.g., by a human hand) to engage a pawl with a suitable groove in the universal strap's groove system.

FIG. 8a is a side cross sectional view of a suction nozzle holster 10 snugly abutting against a rectangular rail 14A. It might also be noted that the desired flexibility of the universal strap 16 is suggested by the fact that said strap 16 can substantially bend around the 90° corner 14B of the rectangular bedrail 14A under a downwardly directed force 72 delivered by a human hand. The ability of a portion 16A of the strap 16 to fit snugly around the corner 14B of the rectangular bedrail 14A illustrates Applicants' previous use of the expression "flexible, universally adjustable strap."

FIG. 8b depicts the lever arm 34 being bent upward to disengage the pawl 36 from a groove in the groove system.

FIG. 8c is a detail of the disengagement of the pawl 36 from a given groove of the groove system 20.

Figure 8D:
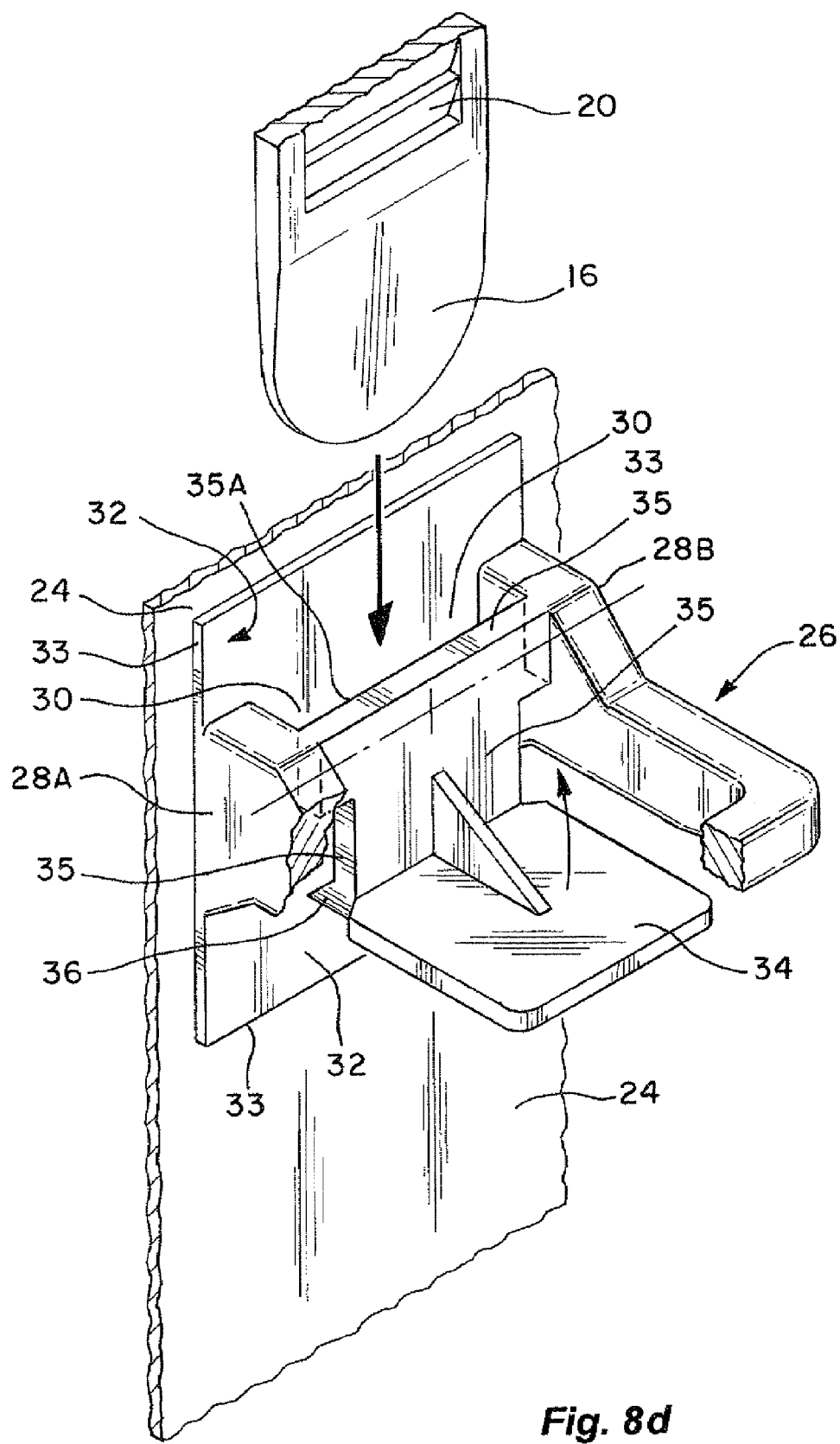
FIG. 8d is an enlarged perspective view of certain components of the first representative latch mechanism.

FIG. 8d is an enlarged detail of a portion of the latch mechanism 26. It particularly details how a rectangular opening 30 is created between the front wall 32 of the plate 33 and rear wall 35A of a vertical element 35. The opening 30 allows passage of the descending universal strap 16 and, consequently, the engagement of a given groove of the groove system 20 with the pawl 36 of the lever arm 34. FIG. 8d also illustrates how the vertical element 35 and lever arm 34 can be comprised of a unitary "L" shaped component that is attached to the side walls 26A and 26B of the latch mechanism 26.

FIG. 9a is a side cross sectional view of a second representative suction nozzle holster device 10 snugly fitting against a round rail 14. Its universal strap 16 is shown: (1) penetrating through a slot 22 in the rear side 24 of the holster component 12, (2) partially encompassing a bedrail 14, (3) provided with a nub configured stop device 68, (4) passing through a rectangular opening 30' in an overhead lever arm post component 31' of a second representative latch mechanism 26' and (5) being held in a state of tension by the engagement of a pawl 36' on the end of the bendable (or rotatable) lever arm 34' of the latch mechanism 26' with a given groove of the groove system 20. The end of the bendable (or rotatable) lever arm 34' is provided with a nub 37' to facilitate finger/thumb gripping of the end of the bendable lever arm 34'.

FIG. 9b is an enlarged detail side view of the second representative latch mechanism 26' that suggests that the bendable (or rotatable) lever arm 34' of the second representative latch mechanism 26' can be temporarily bent upward when a substantially vertically directed human thumb/finger pressure (as suggested by direction arrow 69') is applied to the bottom of the nub 37'. A bending action can also take place at the overhead lever arm post component 31'. This bending (or rotating) action serves to disengage the pawl 36' from a groove of the groove system 20. The bottom portion 34A' of this lever arm 34' can be optionally provided with a roughened surface to prevent thumb/finger slippage during such pressing action. This bending action will be facilitated by the fact that the overhead lever arm post component 31', the vertical plate 33' and the bendable lever arm 34' constitute a unitary piece of suitable elastic, plastic material made by a plastic molding operation.

FIG. 9c is a side detail view of the second representative latch mechanism 26' shown in the absence of the universal strap.

FIG. 9d is a top view of the latch mechanism 26' showing the position of two pivot posts 39A' and 39B' to which the overhead post component 31' (and hence the remainder of the second representative latch mechanism 26') is attached.

FIG. 10a is a side cross sectional view of a suction nozzle holster device 10 snugly fitted against a round rail 14. Its universal strap 16 is shown: (1) penetrating through a slot 22 in the rear side 24 of the holster component 12, (2) partially encompassing a bedrail 14, (3) provided with a nub configured stop device 68, (4) passing through a rectangular opening 30" in a mid post component 31" of a third representative latch mechanism 26" and (5) being held in a state of tension by the engagement of a pawl 36" on the end of a vertically mounted, rotatable lever arm 34" of the this representative latch mechanism 26" with a given groove of the groove system 20.

FIG. 10b is an enlarged detail side view of the third representative latch mechanism 26" that suggests that the pawl 36" on the end of the vertically mounted lever arm 34" of the third representative latch mechanism 26" can be temporarily disengaged from a groove of the groove system 20 when a substantially horizontally directed human thumb/finger pressure (as suggested by direction arrow 69") is applied to the lower end 33" of the lever arm 34" owing to the fact that the vertically mounted lever arm 34" is mounted to pivot posts 37A" and 37B" (not shown). This bottom portion 34A of this lever arm 34 can be optionally provided with a roughened surface to prevent thumb/finger slippage during such pressing action.

FIG. 10c is a side detail view of the third representative latch mechanism 26" shown in the absence of the universal strap.

FIG. 10d is a top view of the third representative latch mechanism 26" showing the position of two pivot posts 37A" and 37B" to which the vertical lever arm 34" (and hence the remainder of the latch mechanism 26") is attached.

FIG. 11a is a side cross sectional view of a suction nozzle holster device 10 snugly fitting against a round rail 14. Its universal strap 16 is shown: (1) penetrating through a slot 22 in the rear side 24 of the holster component 12, (2) partially encompassing a bedrail 14, (3) provided with a nub configured stop device 68, (4) passing through a rectangular opening 30''' in a top plate 31''' of a fourth representative latch mechanism 26''' and (5) being held in a state of tension by the engagement of a pawl 36''' on the bottom end 33''' of a bendable (or rotatable) lever arm 34''' of the fourth representative latch mechanism 26 with a given groove of the groove system 20.

FIG. 11b is an enlarged detail side view of the fourth representative latch mechanism 26''' that suggests that the vertically oriented lever arm 34''' of the fourth representative latch mechanism 26''' can be temporarily bent inward when a substantially horizontally directed human thumb/finger pressure (as suggested by direction arrow 69''') is applied near the center of the lever arm 34'''. The underside of this vertically oriented lever arm 34''' can be provided with a notch to weaken the lever arm 34''' and thereby facilitating bending the lever arm inward and hence disengaging the pawl 36''' from the strap's groove system. This bending action will also be facilitated by the fact that the lever arm 34''' is a unitary piece of suitable elastic, plastic material made by a plastic molding operation.

FIG. 11c is a side detail view of the fourth representative latch mechanism 26''' shown in the absence of the universal strap and shown bent in by a force 69'''.

FIG. 11d is a top view of the latch mechanism 26''' showing the position of two pivot posts 31A''' and 31B''' to which the center post 31''' (and hence the remainder of the latch mechanism 26''') is attached.

Those skilled in this art will appreciate that many other features can be employed in the practice of this invention; consequently the preceding patent disclosure should be regarded as illustrating, but not limiting, the scope of the following claims.

Thus having disclosed this invention, what is claimed is:

1. A medical/dental suction nozzle holster device comprising a holster and a universally adjustable strap that penetrates through a slot in the holster and wherein said strap further comprises a groove system whose individual grooves can engage with a pawl of a lever arm of a latch mechanism that is affixed to an outside rear portion of the holster and wherein the universally adjustable strap further comprises a triangularly configured rear portion whose rear end is thicker than the height of the slot and thereby preventing passage of the strap completely through the slot.

2. The medical/dental suction nozzle holster device of claim 1 wherein the lever arm is vertically mounted.

3. A medical/dental suction nozzle holster device comprising a holster and a universally adjustable strap that penetrates through a slot in the holster and wherein said strap further comprises a groove system whose individual grooves can engage with a pawl of a lever arm of a latch mechanism that is affixed to an outside rear portion of the holster and wherein the universally adjustable strap further comprises a triangularly configured rear portion whose rear end is wider than the length of the slot and thereby preventing passage of the strap completely through the slot.

4. A medical/dental suction nozzle holster device comprising a holster and a universally adjustable strap that penetrates through a slot in the holster and wherein said strap further comprises a groove system whose individual grooves can engage with a pawl of a lever arm of a latch mechanism that is affixed to an outside rear portion of the holster and wherein the universally adjustable strap further comprises a triangularly configured rear portion whose rear end is provided with a stop on each end that respectively come into abutting contact with the end regions of the inside of the slot and thereby preventing passage of the strap completely through the slot.

5. A medical/dental suction nozzle holster device comprising a holster and a universally adjustable strap that penetrates through a slot in the holster and wherein said strap further comprises a groove system whose individual grooves can engage with a pawl of a lever arm of a latch mechanism that is affixed to an outside rear portion of the holster and wherein the universally adjustable strap further comprises a triangularly configured rear portion whose rear end is fused to a perimeter region of the inside of the slot.

6. A medical/dental suction nozzle holster device comprising a holster and a universally adjustable strap that penetrates through a slot in the holster and wherein said strap further comprises a groove system whose individual grooves can engage with a pawl of a lever arm of a latch mechanism that is affixed to an outside rear portion of the holster and wherein the universally adjustable strap further comprises a triangularly configured rear portion whose rear end is glued to a perimeter region of the inside of the slot.

7. A medical/dental suction nozzle holster device comprising: (1) a holster component having a hole for receiving a bent portion of a collapsible suction hose that services a suction nozzle device and (2) a universally adjustable strap component that penetrates through a slot in the holster component and which further comprises a groove system wherein one of its individual grooves can engage with and disengage from a human thumb/index finger operated pawl of a lever arm component of a latch mechanism that is affixed to an outside rear portion of the holster component.

8. The medical/dental suction nozzle holster of claim 7 wherein the universally adjustable strap component further comprises a triangularly configured rear portion whose rear end is thicker than a height of the slot and thereby preventing passage of the strap component completely through the slot.

9. The medical/dental suction nozzle holster of claim 7 wherein the universally adjustable strap further comprises a triangularly configured rear portion whose width is wider than the length of the slot and thereby preventing passage of the strap completely through the slot.

10. The medical/dental suction nozzle holster of claim 7 wherein the flexible, universally adjustable strap further comprises a triangularly configured rear portion whose two upper ends are respectively provided with a stop that comes into abutting contact with the respective end regions of the slot in the holster component.

11. The medical/dental suction nozzle holster device of claim 7 wherein the universally adjustable strap further comprises a triangularly configured rear portion whose rear end is fused to a perimeter region of the inside of the slot.

12. The medical/dental suction nozzle holster device of claim 7 wherein the universally adjustable strap further comprises a triangularly configured rear portion whose rear end is glued to a perimeter region of the inside of the slot.

13. The medical/dental suction nozzle holster device of claim 7 wherein the lever arm is horizontally mounted.

14. The medical/dental suction nozzle holster device of claim 7 wherein the lever arm is vertically mounted.

15. A medical/dental suction nozzle holster device comprising:
- (1) a holster component having:
  - (i) a substantially elliptically configured top lip,
  - (ii) an inwardly and downwardly constricted holster cavity,
  - (iii) a substantially flat region located near the top of the holster component, and
  - (iv) a slot in said substantially flat rectangular region for receiving a universal strap;
- (2) a universally adjustable strap that penetrates through the slot in the holster component and wherein said strap has:
  - (i) a groove system whose individual grooves can engage with and disengage from a human thumb/index finger operated pawl of a lever arm of a latch mechanism, and
  - (ii) a triangular rear portion whose rear end is fused to an inside perimeter region of the slot; and
- (3) a latch mechanism that is attached to the substantially flat region of the holster component and having:
  - (i) a top plate having a rectangular opening through which a leading portion of the universally adjustable strap can pass,
  - (ii) two side walls that form the respective sides of the top plate,
  - (iii) a top plate to which the two side walls are attached,
  - (iv) a base plate to which the side walls are attached and which is affixed to the substantially flat region of the holster component, and
  - (v) a vertical element whose two sides are respectively attached to the two side walls and which respectively lead into and becomes a part of a lever arm having a pawl capable of engaging with a groove of the groove system on the universally adjustable strap.

16. The medical/dental suction nozzle holster device of claim 15 wherein lever arm has a roughened under surface to prevent finger/thumb slippage.

17. A medical/dental suction nozzle holster device comprising:
- (1) a holster component having:
  - (i) a substantially elliptically configured top lip,
  - (ii) an inwardly and downwardly constricted holster cavity,
  - (iii) a substantially flat region located near the top of the holster component, and
  - (iv) a slot in said substantially flat rectangular region for receiving a universal strap;
- (2) a universally adjustable strap that penetrates through the slot in the holster component and wherein said strap has:
  - (i) a groove system whose individual grooves can engage with and disengage from a human thumb/index finger operated pawl of a vertically mounted lever arm of a latch mechanism, and
  - (ii) a triangular rear portion whose rear end is fused to an inside perimeter region of the slot; and
- (3) a latch mechanism that is attached to the substantially flat region of the holster component and having:
  - (i) a post component having a rectangular opening through which a leading portion of the universally adjustable strap can pass, and
  - (ii) a vertically mounted lever arm that is affixed to the post component and further comprising a pawl that is operated by a horizontally directed force on said vertically mounted lever arm.

18. The medical/dental suction nozzle holster device of claim 17 wherein the vertically mounted lever arm has a notched region on its underside.

19. A medical/dental suction nozzle holster device comprising a holster and a universally adjustable strap that penetrates through a slot in the holster and wherein said strap further comprises a groove system whose individual grooves can engage with a pawl of a lever arm of a latch mechanism that is affixed to an outside rear portion of the holster and wherein a hole is provided in a forward surface of the holster.

20. A medical/dental suction nozzle holster device comprising: (1) a holster component having a hole for receiving a bent portion of a collapsible suction hose that services a suction nozzle device and (2) a universally adjustable strap component that penetrates through a slot in the holster component and which further comprises a groove system wherein one of its individual grooves can engage with and disengage from a human thumb/index finger operated pawl of a lever arm component of a latch mechanism that is affixed to an outside rear portion of the holster component and wherein the hole is provided in a forward surface of the holster body.

21. A medical/dental suction nozzle holster device comprising:
- (1) a holster component having:
  - (i) a substantially elliptically configured top lip,
  - (ii) an inwardly and downwardly constricted holster cavity,
  - (iii) a substantially flat region located near the top of the holster component, and
  - (iv) a slot in said substantially flat rectangular region for receiving a universal strap;
- (2) a universally adjustable strap that penetrates through the slot in the holster component and wherein said strap has:
  - (i) a groove system whose individual grooves can engage with and disengage from a human thumb/index finger operated pawl of a vertically mounted lever arm of a latch mechanism, and
  - (ii) a triangular rear portion whose rear end is fused to an inside perimeter region of the slot; and
- (3) a latch mechanism that is attached to the substantially flat region of the holster component and having:
  - (i) a post component having a rectangular opening through which a leading portion of the universally adjustable strap can pass, and
  - (ii) a vertically mounted lever arm that is affixed to the post component and further comprising a pawl that is operated by a horizontally directed force on said vertically mounted lever arm and wherein a hole is provided in a forward surface of the holster component.

* * * * *